United States Patent
McEwen et al.

(10) Patent No.: US 8,137,378 B2
(45) Date of Patent: Mar. 20, 2012

(54) LOW-COST DISPOSABLE TOURNIQUET CUFF APPARATUS AND METHOD

(75) Inventors: James A. McEwen, Vancouver (CA); Michael Jameson, North Vancouver (CA); Kenneth L Glinz, Richmond (CA); Allen J Upward, Vancouver (CA)

(73) Assignee: Western Clinical Engineering, Ltd, Vancouver (CA)

( * ) Notice: Subject to any disclaimer, the term of this patent is extended or adjusted under 35 U.S.C. 154(b) by 1208 days.

(21) Appl. No.: 11/304,363

(22) Filed: Dec. 14, 2005

(65) Prior Publication Data

US 2007/0135835 A1    Jun. 14, 2007

(51) Int. Cl.
*A61B 17/00* (2006.01)
(52) U.S. Cl. ........................................................ 606/203
(58) Field of Classification Search .......... 606/201–203; 128/118.1, 112.1, 95.1; 602/53
See application file for complete search history.

(56) References Cited

U.S. PATENT DOCUMENTS

| | | | | |
|---|---|---|---|---|
| 2,444,161 A | * | 6/1948 | Hanafin | 606/202 |
| 3,504,675 A | * | 4/1970 | Bishop, Jr. | 606/202 |
| 3,670,735 A | * | 6/1972 | Hazlewood | 606/202 |
| 3,892,229 A | | 7/1975 | Taylor | |
| 4,013,069 A | | 3/1977 | Hasty | |
| 4,326,416 A | | 4/1982 | Fredberg | |
| 4,469,099 A | * | 9/1984 | McEwen | |
| 4,479,494 A | * | 10/1984 | McEwen | |
| 4,520,819 A | * | 6/1985 | Birmingham | |
| 4,605,010 A | | 8/1986 | McEwen | |
| 4,635,635 A | * | 1/1987 | Robinette-Lehman | 606/202 |
| 4,979,953 A | * | 12/1990 | Spence | 606/202 |
| 5,125,400 A | * | 6/1992 | Johnson, Jr. | 602/13 |
| 5,193,549 A | | 3/1993 | Bellin | |
| 5,201,758 A | * | 4/1993 | Glover | 606/202 |
| 5,254,087 A | * | 10/1993 | McEwen | |
| 5,312,431 A | | 5/1994 | McEwen | |
| 5,316,002 A | | 5/1994 | Jackson | |
| 5,411,518 A | * | 5/1995 | Goldstein et al. | 606/202 |

(Continued)

OTHER PUBLICATIONS

U.S. Appl. No. 11/153,667, filed Jun. 15, 2005, McEwen.*

(Continued)

*Primary Examiner* — Gary Jackson
*Assistant Examiner* — Erin Colello
(74) *Attorney, Agent, or Firm* — Hancock Hughey LLP

(57) ABSTRACT

Low-cost tourniquet cuff apparatus includes: an inflatable bladder formed of flexible material having a bladder width dimension when the bladder is uninflated and a having a bladder length dimension sufficient for encircling a limb of a surgical patient at a desired location on the limb and for overlapping upon itself, wherein the bladder includes a bladder first inner surface facing a bladder second inner surface along the bladder length dimension and across the bladder width dimension when the bladder is uninflated; securing means for securing the overlapping bladder around the limb at the desired location; port means communicating pneumatically with the inflatable bladder and releasably connectable to a tourniquet instrument for supplying the bladder with pressurized gas; and stiffener means having a predetermined stiffness and having a stiffener width dimension less than the bladder width dimension, wherein the stiffener means is non-releasably attached to the bladder first inner surface within the inflatable bladder. The stiffener means may have a stiffener length dimension that is at least equal to the limb circumference. A method of making the low-cost tourniquet cuff allows the cuff elements to be simply assembled and then sealed in one operation using radio-frequency welding or a similar process.

10 Claims, 5 Drawing Sheets

U.S. PATENT DOCUMENTS

| | | | | |
|---|---|---|---|---|
| 5,413,582 | A | * | 5/1995 | Eaton ............... 606/202 |
| 5,439,477 | A | * | 8/1995 | McEwen |
| 5,445,144 | A | | 8/1995 | Wodicka |
| 5,454,831 | A | * | 10/1995 | McEwen ............ 606/202 |
| 5,556,415 | A | * | 9/1996 | McEwen |
| 5,575,762 | A | | 11/1996 | Peeler |
| 5,578,055 | A | | 11/1996 | McEwen |
| 5,584,853 | A | | 12/1996 | McEwen |
| 5,607,447 | A | | 3/1997 | McEwen |
| 5,649,954 | A | * | 7/1997 | McEwen |
| 5,681,339 | A | * | 10/1997 | McEwen |
| 5,733,304 | A | * | 3/1998 | Spence ............... 606/203 |
| 5,741,295 | A | * | 4/1998 | McEwen ............ 606/202 |
| 5,855,589 | A | | 1/1999 | McEwen et al. |
| 5,904,697 | A | * | 5/1999 | Gifford et al. ......... 606/155 |
| 5,935,146 | A | * | 8/1999 | McEwen |
| 6,009,925 | A | * | 1/2000 | Hall et al. ............. 156/358 |
| 6,506,206 | B1 | | 1/2003 | Guzman |
| 6,537,298 | B2 | * | 3/2003 | Dedo ................ 606/203 |
| 6,682,547 | B2 | * | 1/2004 | McEwen et al. ....... 606/202 |
| 2002/0188315 | A1 | * | 12/2002 | Guzman et al. ....... 606/203 |
| 2003/0167070 | A1 | * | 9/2003 | McEwen |
| 2006/0287672 | A1 | * | 12/2006 | McEwen et al. ....... 606/202 |
| 2007/0135836 | A1 | * | 6/2007 | McEwen et al. ....... 606/203 |
| 2007/0284033 | A1 | * | 12/2007 | Pekar ................ 156/273.7 |

OTHER PUBLICATIONS

U.S. Appl. No. 11/198,565, filed Aug. 5, 2005, McEwen.*
U.S. Appl. No. 11/219,016, filed Sep. 1, 2005, McEwen.*
U.S. Appl. No. 11/346,846, filed Feb. 2, 2006, McEwen.
International Preliminary Report on Patentability issued in corresponding International Application PCT/CA2006/002008; Jun. 26, 2008; 7 pages.

* cited by examiner

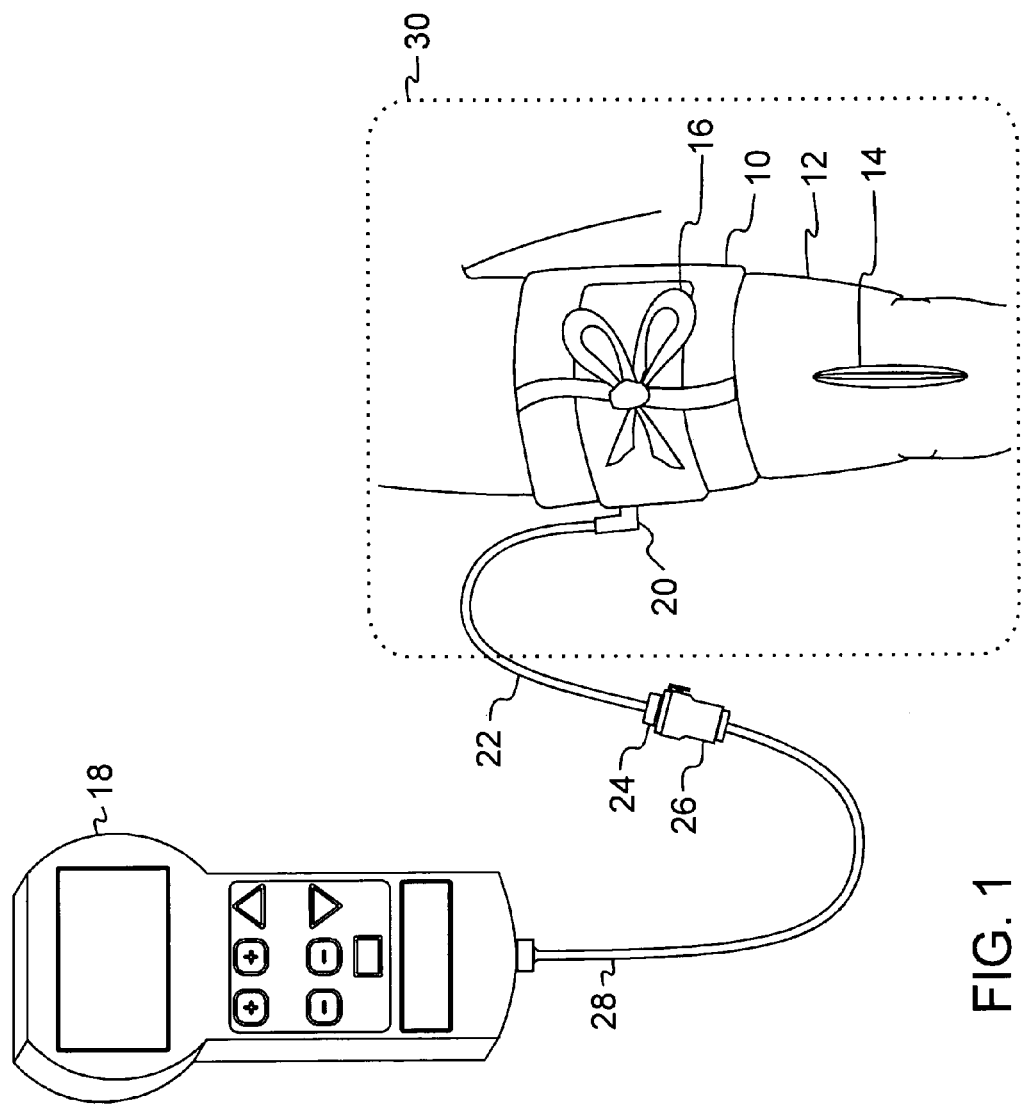

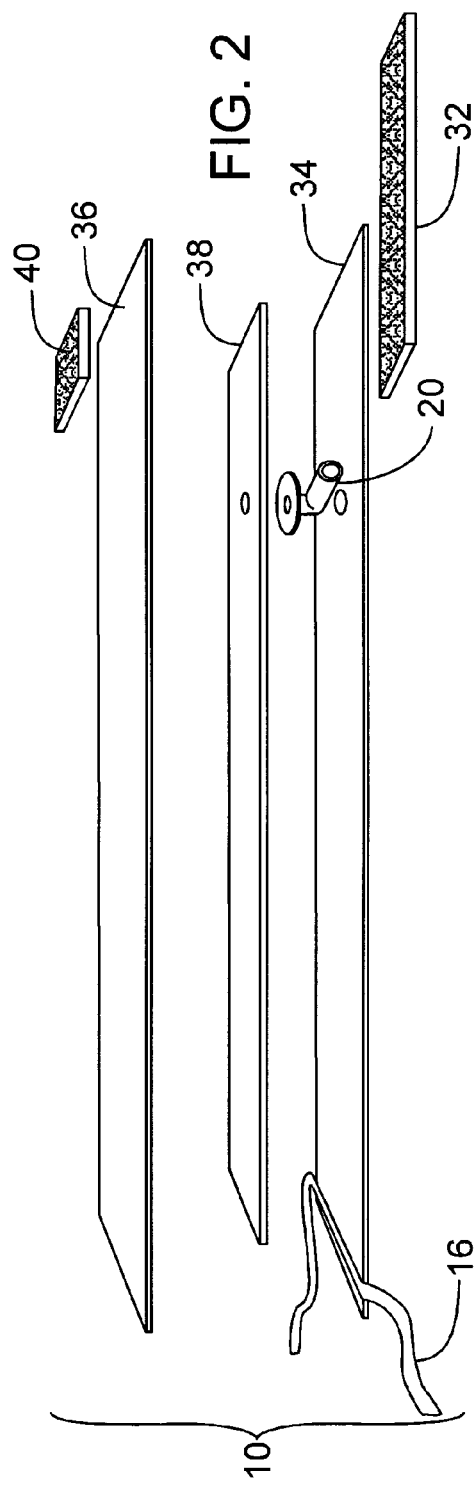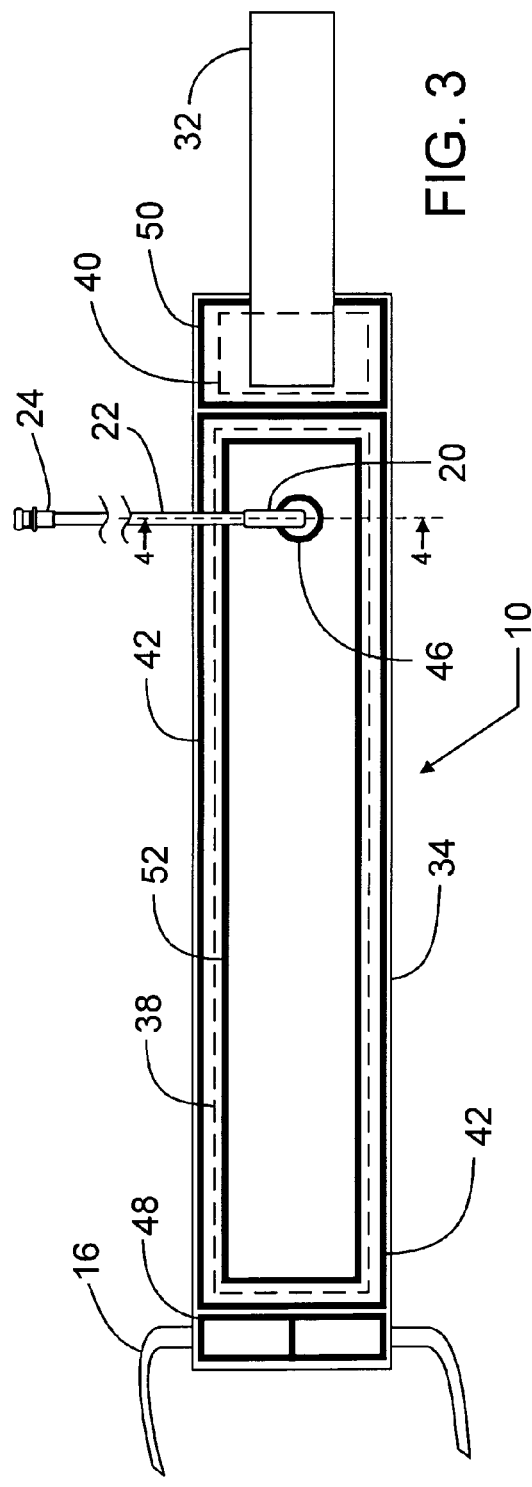

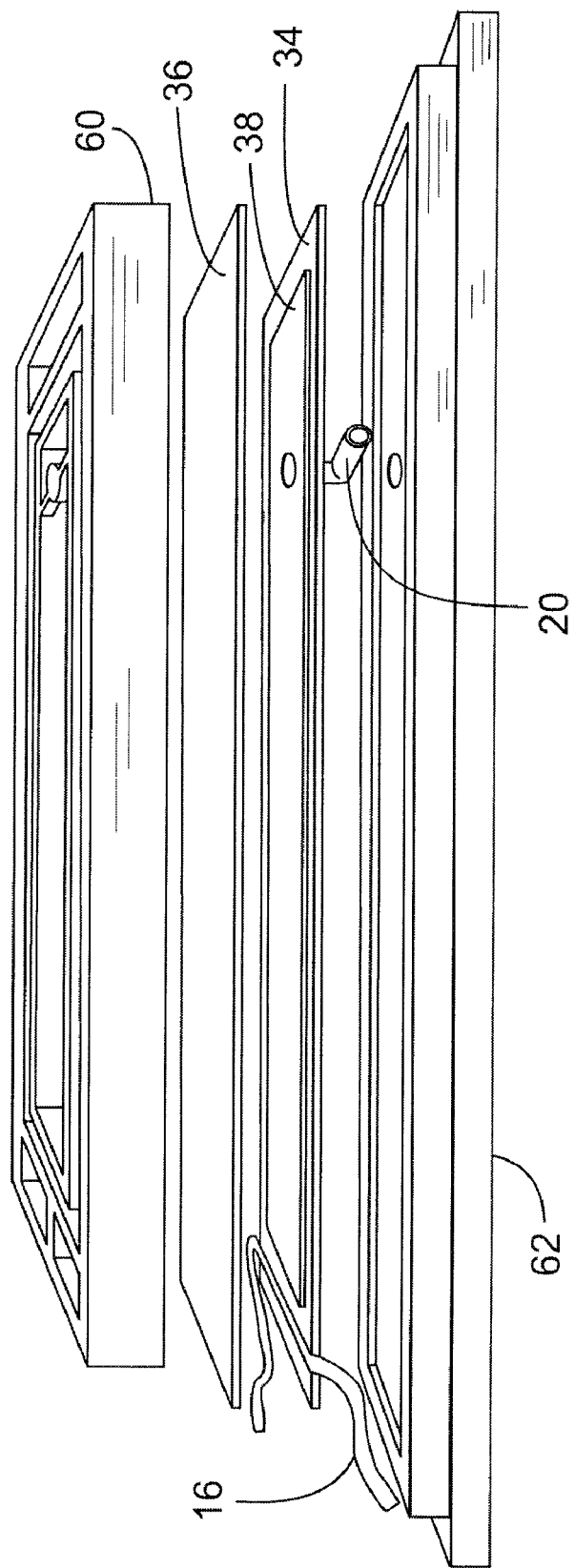

LOW-COST DISPOSABLE TOURNIQUET CUFF APPARATUS AND METHOD

FIELD OF THE INVENTION

This invention pertains to pneumatic tourniquet cuffs commonly used for stopping arterial blood flow into a portion of a surgical patient's limb to facilitate the performance of a surgical procedure, and for facilitating intravenous regional anesthesia.

BACKGROUND OF THE INVENTION

Typical surgical tourniquet systems of the prior art include a tourniquet cuff which encircles the limb of a surgical patient, and a tourniquet instrument which is releasably connected to the tourniquet cuff through a length of tubing, establishing a sealed gas passageway between the cuff and instrument. Tourniquet cuffs typically include an inflatable portion, which encircles the limb of a patient at a desired location, and is connected through a cuff port to a tourniquet instrument through one or more sections of tubing.

The tourniquet instrument contains a pressurized gas source which is used to inflate and regulate the pressure in the tourniquet cuff above a minimum pressure required to stop arterial blood flow distal to the cuff, for a duration suitably long for the performance of a surgical procedure. Many types of surgical tourniquet systems have been described in the prior art, such as those described by McEwen in U.S. Pat. Nos. 4,469,099, 4,479,494, 5,439,477 and McEwen and Jameson in U.S. Pat. Nos. 5,556,415 and 5,855,589.

A number of different types of disposable tourniquet cuffs are known in the prior art. These cuffs are intended to be used within sterile surgical fields, and are typically sterilized at the time of manufacture. Examples of multi-layer disposable cuffs in the prior art are described by Robinette-Lehman in U.S. Pat. No. 4,635,635, and in commercial products manufactured in accordance with its teachings ('Banana Cuff' sterile disposable tourniquet cuffs, Zimmer Arthroscopy Systems, Englewood Colo.), and by Guzman et al. in U.S. Pat. No. 6,506,206, and in commercial products manufactured with its teachings ('Comfortorm™ Disposable Gel Cuff', DePuy Orthopaedics Inc., Warsaw Ind.). A two-layer disposable cuff of the prior art is described by Spence in U.S. Pat. No. 5,733,304. Disposable cuffs of the prior art tend to be constructed using exotic materials, such as gel layers, and large amounts of of materials, such as multi-layer cloth/thermoplastic laminates, which are expensive . Also, the use of these materials in prior-art cuffs has tended to result in a greater overall cuff thickness and stiffness, making the cuffs difficult to apply consistently. Thicker and stiffer cuffs of the prior art may also degrade performance after cuff application so that higher tourniquet pressures may be required to reliably occlude blood flow; this is undesirable because higher tourniquet pressures are associated in the surgical literature with a higher risk of patient injury.

Typical tourniquet cuffs of the prior art include a sealed bladder which encircles the limb and which communicates pneumatically with a connected tourniquet instrument through one or more gas passageways, a stiffener to help direct the expansion of the cuff bladder radially inwards towards the limb and to help prevent twisting of the cuff and rolling of the cuff along the limb, and one or more fasteners for securing the cuff around the limb.

In order to facilitate the attachment of fasteners and the establishment of gas passageways to the cuff, the assembly process is completed in several labor-intensive operations, some of which require a high level of skill. These operations can include sewing fastener materials to the outer cuff layer, adding a structural reinforcing patch to the outer layer, sealing the port to the bladder layer, and sealing the bladder perimeter.

Cuff layers consisting of compatible thermoplastic polymeric materials are typically joined together using a radio frequency (RF) welding process, which uses a combination of heat and pressure to cause compatible polymers to flow together by molecular diffusion. Welding operations to make cuffs of the prior art are typically completed in multiple steps, each of which typically requires operator intervention. Cuff layers are positioned in a bottom die plate, and then engaged against a top die plate by a pneumatic press. A typical tourniquet cuff of the prior art requires at least two welding operations to form the bladder.

The bladder is typically formed from two separate sheets of thermoplastic coated material and sealed around a perimeter using an RF welding process. The gas passageways into the bladder are formed through single or multiple port flanges, which are sealed through the bladder using the RF welding process. The port provides a reinforced structure which is attached to tubing that extends outside the sterile surgical field for connection to a tourniquet instrument. The port flange is sealed to a single side of the bladder in a separate operation, to prevent the opposite bladder surface from bonding at the port location. The bladder seal is usually completed in a single operation, after the attachment of one or more ports, and lies around the perimeter of the cuff close to the edges.

Tourniquet cuffs of the prior art typically include a thermoplastic stiffener element, which helps direct the expansion of the cuff bladder radially inward towards the limb when pressurized, and helps reduce the tendency of the cuff to twist when pressurized and to roll along a tapered limb. The absence of an internal stiffening element leads to a reduction of the efficient application of pressure to the limb, and thus leads to an increase in the level of pressure required to stop blood flow past the cuff and into the limb. Also, the absence of a stiffening element would lead to additional stresses in the outer cuff surface due to less constrained bladder expansion. To help direct expansion of the cuff bladder, tourniquet cuffs of the prior art contain a stiffener element in one of several configurations. The first, most widely used type of stiffener configuration contains a non-inflating sheath which houses the stiffener outside the inflatable bladder (as in Zimmer ATS sterile disposable tourniquet cuffs distributed by Zimmer Inc., Dover Ohio). This method of constraining the stiffener facilitates the inward expansion of the cuff into the soft tissues of the limb encircled by the cuff when the cuff is pressurized, and provides resistance to twisting and rolling. It also results in a cuff that is thinner than other pre-art cuffs, which reduces wrinkling on the inner surface of the cuff caused by differences of circumference between the inner and outer cuff surfaces.

A second type of stiffener configuration in cuffs of the prior art involves increasing the thickness and rigidity of the outer cuff material layer, to obtain a stiffening function from the outer layer in a two-layer cuff design (as described by Eaton in U.S. Pat. No. 5,413,582, and in cuffs distributed by Oak Medical, Briggs, North Lincs, UK,). The outer layer of these prior-art cuffs serves both as a stiffener and as one side of the inflatable bladder. The thick outer layer extends to all the cuff edges, and includes an area for sealing the inner layer to the thick outer layer to form the bladder, resulting in the bladder always having a width that is less than the width of the stiffener; this is undesirable because cuffs having narrower bladder widths require higher tourniquet pressures to stop blood flow, and higher tourniquet cuff pressures are associated with a higher risk of patient injury. Also, this second type of stiffener configuration in cuffs of the prior art, in which the stiffener forms part of the inflatable bladder, greatly limits the extent to which the cuff can expand inwardly into soft tissue when the cuff is pressurized; this limitation increases the pressure required to stop or occlude blood flow in the encircled limb, especially in obese patients and patients having large amounts of soft tissue. Further, the thick and stiff edges formed at the side edges of these prior-art cuffs may have a tendency to buckle towards the limb, leading to a potential soft-tissue hazard.

A third stiffener configuration in tourniquet cuffs of the prior art consists of an unsecured stiffener placed within the inflatable bladder (for example, as described by Spence in U.S. Pat. No. 5,733,304, by Goldstein et al. in U.S. Pat. No. 5,411,518, and as seen in 'Color Cuff II' sterile disposable tourniquet cuffs distributed by InstruMed Inc., Bothell Wash.). In this configuration, the stiffener is unsecured within the bladder and does not constrain the expansion of the outer cuff surface. This reduces the effectiveness of the stiffener in directing cuff pressure toward the encircled limb across the width of the cuff, and it reduces the extent to which the cuff can expand inwardly when pressurized, thereby making its performance more sensitive to variations in application technique and thereby leading to the possible need for higher tourniquet pressures to stop blood flow past the cuff and into the limb, particularly in patients having large amounts of soft tissue and in patients with poor muscle tone. Further, an unsecured stiffener within the cuff bladder is not as effective as a secured stiffener in helping to prevent the cuff from twisting or rolling axially along the limb. In addition, in order to reduce the limitations of performance that are inherent in a cuff having an unsecured stiffener within the inflatable bladder, the width of the stiffener in prior art cuffs has been increased to be as close as possible to the bladder width, which impairs cuff performance and which requires precise alignment of the stiffener during manufacture.

Cuffs of the prior art typically employ hook and loop type fastener elements, which are attached to the outer layer of the cuff. The most common configuration consists of a hook-type strap which wraps around and engages with a loop-type material, which is contained by the outer surface of the cuff.

In general, it is desirable to construct the thinnest tourniquet cuff possible for a given application, to reduce wrinkles on the inner cuff surface and to allow the user to apply the cuff snugly to the limb. Drawbacks associated with thicker, more rigid cuff materials are discussed above, and many are caused by prior art attempts to combine several cuff elements into a single composite material. This often results in an increase in thickness and overall rigidity, and a compromise in cuff performance.

Many cuffs of the prior art are susceptible to partial or complete blockage of the gas passageways communicating with the tourniquet cuff. Occlusion of the gas passageways can occur in several typical scenarios, including either kinking the hose leading from the port connection, and pressing the port flange against the lower bladder surface isolating the port passageway from the bladder, either of which can inhibit the accurate sensing and regulation of pressures within the tourniquet cuff. Several anti-occlusion apparatus are described by McEwen et al. in U.S. patent application Ser. No. 11/153,667.

The manufacturing and assembly process of prior art cuffs consists of numerous cutting, sewing, and sealing operations which require substantial investment in both equipment and skilled operators. The manual labor component of cuff assembly is high, especially where multiple sewing and sealing operations are required. It is therefore desirable to reduce the skill and time required by the cuff assembly process, while continuing to utilize readily available manufacturing equipment.

A reduction in the amount of time and skill required to build a tourniquet cuff can be accomplished by reducing the number of manual assembly operations. This may include the elimination of numerous sewing operations, and the consolidation of multiple RF sealing steps into a single operation. Reducing the number of manual operations provides a savings not only in the labor to construct a cuff, but also provides the potential for the automation of a number of steps leading to the single cuff sealing operation.

In U.S. Pat. No. 6,682,547 McEwen et al. describe a method for automating the cuff manufacturing process by constructing the top layer sheet of the cuff in a continuous strip with the middle of the sheet of one thickness, tapering down at the side edges. This allows the top layer of the cuff to provide the stiffening functions described previously, while not limiting the inward radial reach of the bladder. McEwen et al. describe a custom manufacturing process which allows the bottom and top sheet material to be joined in a continuous process, whereby the edge of the inner layer is folded over the outer layer and sealed. The end edges of the cuff are sealed at various intervals to allow the construction of cuffs of a variety of lengths. The stiffened top layer therefore extends to the ends of the resulting cuff.

While manufacturing a tourniquet cuff using the design and methods described in the '547 patent may result in a high potential level of automation, the cost of creating the custom manufacturing equipment required to would be high, due to the limited similarities which exist with currently employed cuff manufacturing equipment. It is therefore desirable to use as much of possible of current cuff manufacturing infrastructure.

There is a need for tourniquet cuff apparatus which can overcome the limitations, problems and hazards of cuff performance that are described above, and for tourniquet cuff apparatus that can be manufactured using existing infrastructure, at lower cost from less materials and from inexpensive materials, with a reduced number of operations and with a reduction in the level of operator skill required.

BRIEF DESCRIPTION OF THE DRAWINGS

FIG. 1 is a pictorial representation of the preferred embodiment in a surgical application.

FIG. 2 is an exploded view of the preferred embodiment.

FIG. 3 is a top view of the preferred embodiment.

FIG. 5 shows the preferred embodiment positioned within a dielectric welding die.

DETAILED DESCRIPTION OF THE PREFERRED EMBODIMENT

Figure 4A:
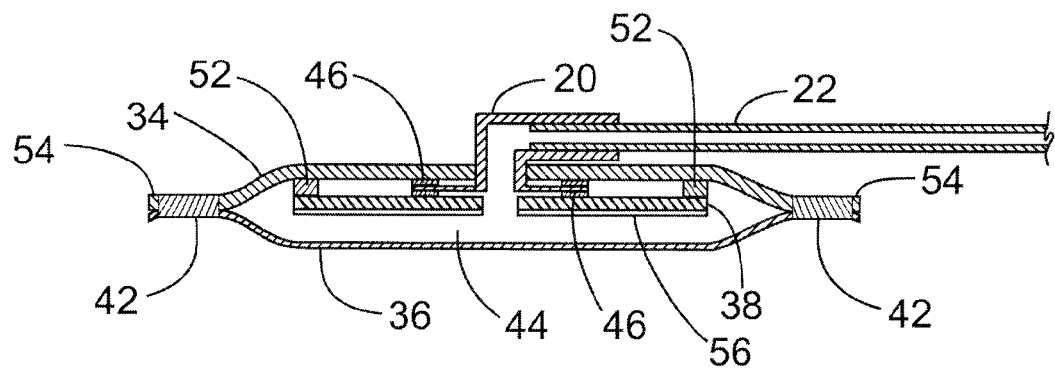
FIGS. 4a, 4b and 4c are section views taken from FIG. 3.

FIG. 1 is a pictorial representation of the preferred embodiment in a surgical application, showing tourniquet cuff 10 secured circumferentially around patient limb 12 proximal to surgical site 14. Tie strap 16 described further below, is tied as shown in FIG. 1 to help prevent the cuff 10 from sliding proximally or distally on limb 12 when cuff 10 is inflated.

The inflatable portion of tourniquet cuff 10 completely encircles patient limb 12 and is pneumatically connected to tourniquet instrument 18 via cuff port 20, cuff tubing 22, cuff connector 24, instrument connector 26 and instrument tubing 28. Tourniquet instrument 18 supplies pressurized gas for the inflation of cuff 10 and is capable of inflating cuff 10 to a pressure that will occlude the flow of arterial blood in patient limb 12 distal to cuff 10.

The perimeter of a sterile surgical field 30 encloses surgical site 14, a portion of patient limb 12, tourniquet cuff 10, and a portion of cuff tubing 22. Cuff tubing 22 is of sufficient length to permit cuff connector 24 to be releasably mated with instrument connector 26 outside of sterile surgical field 30. In the preferred embodiment shown, cuff 10 is a single port cuff, where cuff port 20 provides a single pneumatic passageway into the inflatable portion of cuff 10. Those skilled in the art will appreciate that the features described in the preferred embodiment may also be applied to tourniquet cuffs having more than one port, such as those described by U.S. Pat. Nos. 4,469,099, 4,479,494, and 5,254,087.

As described below, cuff 10 is constructed of materials that are appropriate for a single-use sterile disposable tourniquet cuff. To permit cuff 10 to be used in a sterile surgical field, cuff 10 is sterilized at time of manufacture by exposure to a sterilizing agent within a sterilizing process determined to be safe and effective. To prevent deterioration of the cuff, and to maintain the integrity of the pneumatic passageways within cuff 10, a sterilization agent and process that will not harm the materials or components of cuff 10 is selected by the manufacturer. In the preferred embodiment cuff 10 is sterilized by exposure to gamma radiation or electron beam radiation.

The cost of materials and labor are important considerations in the manufacture of tourniquet cuffs intended for a single use and then disposal. To minimize the cost of materials and assembly of cuff 10, materials are selected which are not intended to withstand exposure to subsequent sterilization and cleaning processes. The subsequent sterilization or cleaning of cuff 10 by agents and processes commonly used in health care facilities, such as ethylene oxide gas sterilization, hydrogen peroxide gas sterilization, high temperature and pressure steam sterilization, sterilization by other chemical agents, and pasteurization, are all capable of adversely affecting the integrity of the materials and pneumatic passageways of cuff 10. As described in pending U.S. patent application Ser. No. 11/198,565 and herein incorporated by reference, cuff tubing 22 acts as a visual indicator to warn a user that cuff 10 has been subjected to a subsequent sterilization or cleaning process capable of adversely affecting cuff 10 and that cuff 10 may no longer be safe to use. Cuff 10 may be manufactured with an internal usage register as described in U.S. patent application Ser. No. 11/219,016 and herein incorporated by reference, for limiting the usage of cuff 10 to usage within safe usage limits, and to usage in only one surgical procedure.

To prevent occlusion of the pneumatic passageway within cuff tubing 22, cuff tubing 22 has a cross sectional profile as described in pending U.S. patent application Ser. No. 11/153,667 and herein incorporated by reference, that prevents complete occlusion of the pneumatic passageway within cuff tubing 22 if tubing 22 is kinked or flattened.

FIG. 2 is an exploded view of the individual components that are joined together as described below to form cuff 10. For clarity, cuff tubing 22 and cuff connector 24 are not shown in FIG. 2.

Those skilled in the art will appreciate that many conventional methods exist for joining the thermoplastic polymers that comprise the materials of cuff 10. Joining processes can be separated into two broad groups: adhesive bonding, and thermal or solvent welding. In an adhesive bonding process, an adhesive layer is applied between two or more materials and when cured, the adhesive holds the materials together at their surfaces. In a thermal or solvent welding process, the surfaces of two or more materials are made fluid by applying either thermal heating or a solvent, which allow the thermoplastic materials to molecularly diffuse into one another forming a weld. For molecular diffusion to occur the thermoplastic polymers being thermally or solvent welded must be sufficiently compatible. Thermal or solvent welding will not occur between incompatible materials, for example, polyurethane and polyethylene. Thermal welding can be accomplished by numerous methods, including direct heating (e.g., hot gas, infrared, extrusion), induced heating (e.g., radio frequency (RF) or dielectric welding), and frictional heating (e.g., ultrasonic welding). In the preferred embodiment and as described below, the thermoplastic polymers comprising components of cuff 10 are joined together by the dielectric welding process, in which materials are brought together under pressure in a die, radio frequency energy is applied to temporarily melt a portion of the thermoplastic materials causing them to weld together in a selected area. Dielectric welding relies on the principle of dielectric heating to in induce heat in thermoplastic materials placed within an alternating electromagnetic field. The amount of potential heating generated is dependent upon the dielectric properties of the thermoplastic materials, known as loss factor or dissipation factor. Thermoplastics with a relatively high dissipation factor such as polyurethane can be readily dielectrically welded, while thermoplastics with low dissipation factors such as polyethylene can not be readily welded by this process. While thermoplastic polyethylene will not heat substantially during the dielectric welding process it will still provide a conductive path through which the alternating electromagnetic field will propagate allowing welding to occur in adjacent materials.

To reduce manufacturing equipment and labor costs it is desirable to manufacture cuff 10 in a single dielectric welding operation. This requires that the thermoplastic polymers comprising the components of cuff 10 be prevented from welding at selected surfaces. Preventing thermoplastic materials from welding together can be accomplished by several methods. One method involves coating the surface of a thermoplastic material with a material that prevents the molecular diffusion into another otherwise compatible material. Another method involves selecting thermoplastic materials that have markedly different dissipation factors, preventing one or more of the materials from heating during a dielectric welding operation. As described above, both methods may be employed in the manufacture of cuff 10.

Referring to the components of cuff 10 shown in FIG. 2, securing strap 32 is made of a hook material that is commonly used in "hook and loop" fastening applications. In use, securing strap 32 engages with loop material on the outer surface of top sheet 34. When cuff 10 is applied to a limb, securing strap 32 is engaged by a user to the loop material of top sheet 34 to secure cuff 10 circumferentially around the limb. The length and specifications of the hook material comprising securing strap 32 are selected to maintain cuff 10 securely around the limb circumference when cuff 10 is inflated.

Top sheet 34 is a thin flexible nylon loop material adapted for secure engagement with the hook material of securing strap 32. Top sheet 32 is coated on the inner surface with a thermoplastic polymer. This thermoplastic polymer coating prevents the passage of gas through top sheet 34 and allows top sheet 34 to be joined to cuff port 20, bottom sheet 36 and to stiffener 38 as described below. In the preferred embodiment the thermoplastic coating on top sheet 34 is polyurethane.

Bottom sheet 36 is made of flexible woven cloth coated on the inner surface with a thermoplastic polymer. The thermoplastic polymer coating prevents the passage of gas through bottom sheet 36 and allows bottom sheet 36 to be joined to top sheet 34 as described above and below. In the preferred embodiment the thermoplastic coating on bottom sheet 36 is polyurethane. It will be appreciated by those skilled in the art that other thermoplastic polymers, polyvinylchloride for example, may be used as coatings on top sheet 34 and bottom sheet 36 providing they can be joined with sufficient strength to maintain the integrity of cuff 10 when inflated.

As shown in FIG. 2, cuff port 20 has a right angle configuration and includes a flange. Cuff port 20 is made of a thermoplastic polymer that is compatible with and can be joined to the thermoplastic coating of top sheet 34 to form a gas tight seal.

Tie strap 16 is a soft fabric ribbon material that is shown in FIG. 2 positioned between bottom sheet 36 and top sheet 34. As described below, tie strap 16 is secured between top sheet 34 and bottom sheet 36. Tie strap 16 provides a means for the user to pull cuff 10 snug around the limb and when tied as shown in FIG. 1, helps prevent the inflated cuff from sliding proximally or distally on the limb.

Secondary fastener 40 is hook material similar to the hook material that comprises securing strap 32. Secondary fastener 40 is attached to the outer surface of bottom layer 36 and engages with the loop material of top sheet 34 to help maintain cuff 10 secured around a limb. Secondary fastener 40 also acts as an aid for the user when applying cuff 10 to a limb by providing a means to temporarily maintain cuff 10 secured in position around a limb while securing strap 32 is engaged.

Stiffener 38 is made of a thermoplastic polymer sheet cut to a rectangular shape to fit within the perimeter of bladder perimeter weld 42 shown in FIG. 3. Top sheet 34 and bottom sheet 36 are welded together at bladder perimeter weld 42 to form an inflatable bladder 44 shown in FIGS. 4*a*, 4*b*, and 4*c*.

Stiffener 38 has a greater stiffness and is less flexible than top sheet 34 and bottom sheet 36 but is flexible enough to be wrapped around a limb (for example, 0.020" thick polyurethane/polyvinylchloride alloy sheet or polyethylene sheet). When secured circumferentially around the limb as shown in FIG. 1, stiffener 38 helps direct the expansion of inflatable bladder 44 radially inwards towards the limb upon inflation of cuff 10. The stiffener thus provides uniformly distributed pressure onto limb. Attaching stiffener 38 to top sheet 34 prevents top sheet 34 from moving relative to stiffener 38 and thereby helps prevent cuff 10 from "rolling" down patent limb 12 when cuff 10 is inflated. The attachment of stiffener 38 to top layer 34 permits the use of thin flexible materials for top sheet 34 and bottom sheet 36 making for a thinner overall cuff which is desirable as thin cuffs afford an improved fit to .the patient limb with less wrinkling of materials. Some prior art cuffs with a stiffener floating within the bladder use heavier stiffer materials for the bladder walls to resist "rolling" on the limb. These thick materials result in more wrinkling of the bladder surfaces when the cuff is applied to the limb.

The width of stiffener 38 is less than the width of inflatable bladder 44 when cuff 10 is laid flat. The width of stiffener 38 determines the degree to which bladder 44 can expand (or reach) to apply pressure into the limb. Unlike prior art cuffs that have a stiffener extending beyond the width of the inflatable bladder, cuff 10 has greater reach and thereby results in lower limb occlusion pressures than those obtainable with prior art cuffs. In the preferred embodiment a surface of the thermoplastic polymer that comprises stiffener 38 is compatible with the thermoplastic coating of top sheet 34 and is welded to the inner surface of top sheet 34 by the dielectric welding process described above. Stiffener 38 is prevented from welding to the inner surface of bottom sheet 36 by an incompatible coating which is applied as described below to either to a surface of stiffener 38 or to a portion of the inner surface of bottom sheet 38.

FIG. 3 is a top view of the preferred embodiment laid flat showing the areas where the inner surface of top sheet 34 are welded to bottom sheet 36, cuff port 20 and stiffener 38. The separate weld areas shown in FIG. 3 are: bladder perimeter weld 42, cuff port weld 46, tie strap retaining weld 48, non-inflating region weld 50, and stiffener retaining weld 52. Bladder perimeter weld 42 defines inflatable bladder 44 of cuff 10. Cuff port 20, cuff tubing 22 and cuff connector 24 provide a pneumatic passageway communicating with inflatable bladder 44 through which bladder 44 may be inflated.

In FIG. 3, securing strap 32 is shown attached to the top surface of cuff 10, in the preferred embodiment securing strap 32 is sewn to a non-inflating region of cuff 10 within the perimeter of non-inflating region weld 50 and secondary fastener 40 is sewn to the bottom surface of cuff 10 opposite the attachment point of securing strap 32. Alternatively, bladder perimeter weld 42 may be extended to the end edge of cuff 10 thereby eliminating the non-inflating region weld 50. Secondary fastener 40 can then be attached to the bottom surface of cuff 10 with adhesive and the length of securing strap 32 can be increased to permit greater engagement with the surface of top sheet 34.

Tie strap 16 is permanently attached to cuff 10 by tie strap weld 48 shown in FIG. 3. Top sheet 34, tie strap 16, and bottom sheet 36 are joined together at tie strap weld 48 which acts to retain tie strap 16 to cuff 10.

Figure 4B:
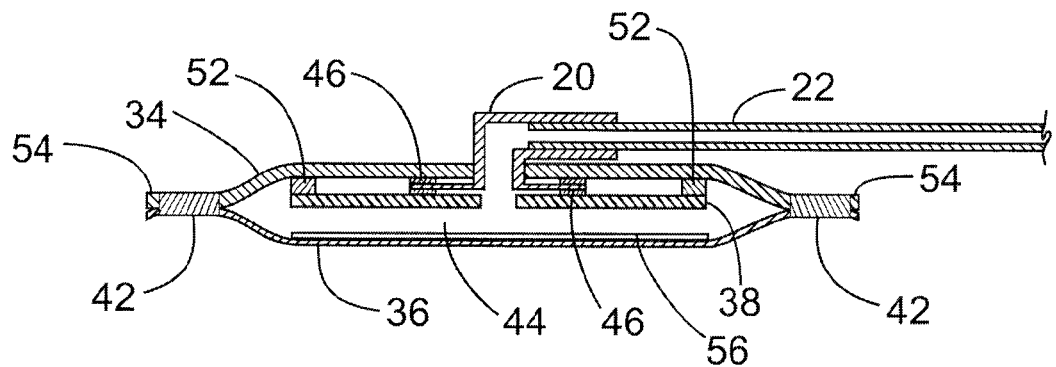
Figure 4C:
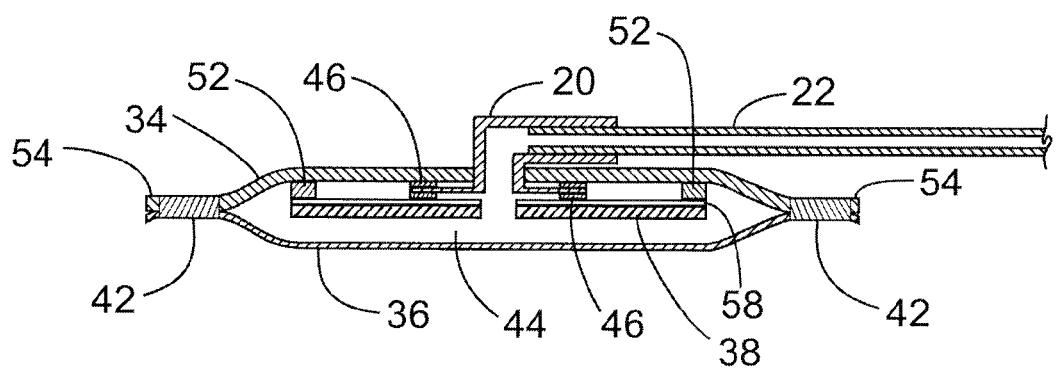

Cross section 4 of cuff 10 is shown in FIG. 4*a*, 4*b* and 4*c*. FIGS. 4*a*, 4*b* and 4*c* depict the regions where surfaces of the components of cuff 10 are joined together by welds and show alternate methods for preventing selected surfaces of the components of cuff 10 from forming welds during the welding process.

Referring to FIG. 4*a*, top sheet 34 is joined to bottom sheet 36 at bladder perimeter weld 42 forming inflatable bladder 44. In the preferred embodiment bladder perimeter weld 42 does not extend to the longitudinal side edges of top sheet 34 and bottom sheet 36 thereby leaving a non-welded edge 54 along the length of cuff 10. This non-welded edge provides a softer more compliant edge for patient comfort than can be obtained when the width of the bladder perimeter weld extends completely to the side edges of top sheet 34 and bottom sheet 36.

Cuff port 20 is joined to the inner surface of top sheet 34 and outer surface of stiffener 38 at the location of cuff port weld 46.

As shown in FIG. 3, stiffener securing weld 52 is formed around the perimeter of stiffener 38 and acts to non-releasably attach the outer surface of stiffener 38 to the inner surface of top sheet 34, thereby preventing stiffener 38 from moving relative to top sheet 34 when cuff 10 is inflated.

As shown in FIG. 4*a* the thermoplastic polymer of stiffener 38 is compatible with the thermoplastic coating on the inner surface of top sheet 34 and the two surfaces can be welded to each another. To permit cuff 10 to be manufactured in a single dielectric welding operation, a barrier 56 is applied to the inner surface of stiffener 38. Barrier 56 is a coating of thermoplastic material (for example polyethylene) that is not compatible with the thermoplastic coating on the inner surface of bottom sheet 36 and acts to prevent stiffener 38 from welding to the thermoplastic coating on the inner surface of bottom sheet 36 at the location of stiffener securing weld 52 and cuff port weld 46.

The cross section 4 of cuff 10 shown in FIG. 4b illustrates an alternate location for barrier 56. As shown in FIG. 4b barrier 56 is applied to a region of the inner surface of bottom sheet 36 such that stiffener 38 is prevented form welding with the thermoplastic coating on the inner surface of bottom sheet 36 at the location of stiffener securing weld 52 and cuff port weld 46.

In the alternate embodiment depicted in FIG. 4c, stiffener 38 is formed from a thermoplastic which will not weld with the thermoplastic coatings on top sheet 34 and bottom sheet 36, such as polyethylene. To permit a stiffener made of an incompatible thermoplastic to be attached to the inner surface of top sheet 34, a stiffener coating 58 of a compatible thermoplastic such as polyurethane is laminated to the outer surface of stiffener 38. This laminated coating allows stiffener 38 to be non-releasably attached to the inner surface of top sheet 34.

FIG. 5 shows bottom sheet 36, top sheet 34, stiffener 38, cuff port 20 and tie strap 16 positioned between an upper sealing die 60 and a lower sealing die 62. As described above, a single dielectric welding operation may be used to manufacture cuff 10. To manufacture cuff 10 in a single welding operation, cuff port 20 is inserted through an opening in top sheet 34 such that the flange on cuff port 20 engages the inside surface of top sheet 34. Stiffener 38 is then positioned on top sheet 34 such that stiffener 38 will not overlap bladder perimeter weld 42. Top sheet 34 with cuff port 20 and stiffener 38 is positioned in lower sealing die 62. Tie strap 16 is positioned at an end edge of top sheet 34 and bottom sheet 36. Bottom sheet 36 is then positioned on top of stiffener 38 such that the thermoplastic coating faces stiffener 38. When the two halves of the sealing die are brought together under pressure and radio frequency energy is applied, top sheet 34 is welded to bottom sheet 36 at the location of bladder perimeter weld 42 shown in FIG. 3; cuff port 20 is welded to the inner surface of top sheet 34 and to the outer surface of stiffener 38 at the location of cuff port weld 46; tie strap 16 is bonded to the inner surfaces of top sheet 34 and bottom sheet 36 at the location of tie strap weld 48; and the outer surface of stiffener 38 is welded to the inner surface of top sheet 34 at stiffener securing weld 52 as shown in FIG. 3.

Figure 6:
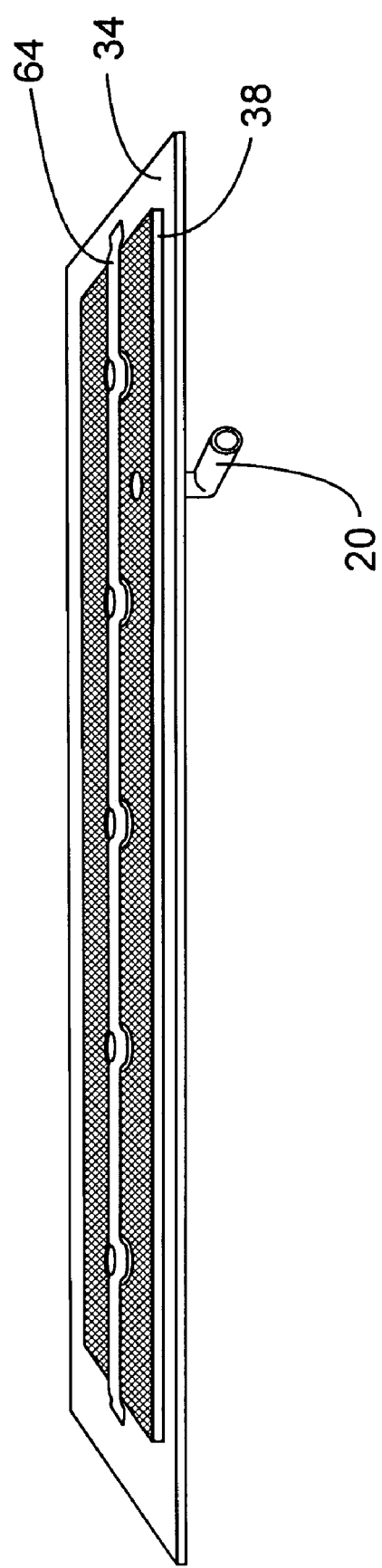
FIG. 6 depicts an alternate method for the non-releasable attachment of the stiffener to the top sheet of the preferred embodiment.

FIG. 6 depicts an alternate method for non-releasably attaching stiffener 38 to the inner surface of top sheet 34. Stiffener retaining strip 64 is a strip of thermoplastic coated cloth, similar to top sheet 34 described above. Stiffener retaining strip 64 is welded to top sheet 34 at the end edges of stiffener 38 and to top sheet 34 through a series of openings in stiffener 38. Stiffener retaining strip 64 thereby non-releasably attaches stiffener 38 to top sheet 34 and prevents stiffener 38 from moving significantly relative to top sheet 34. The size of the openings in stiffener 38 through which stiffener retaining strip 64 is welded relative to the size of the weld bonding stiffener retaining strip 64 to top sheet 34 controls the degree to which stiffener 64 is free to move in relation to top sheet 34. The openings and weld areas can be sized to allow stiffener 38 to move longitudinally relative to top sheet 34 if desired. For cuffs designed for large limb circumferences, allowing stiffener 38 to move in this fashion may allow cuff 10 to be more tightly coiled for packaging prior to sterilization. The surfaces of stiffener retaining strip 64 may be selected such that one surface welds to the inner surface of top sheet 34 while the opposite surface does not weld to the inner surface of bottom sheet 36 thereby permitting cuff 10 to be manufactured in a single dielectric sealing operation if desired.

It will also be appreciated that stiffener 38 may be non-releasably attached to the inner surface of top sheet 34 by an adhesive bond by selecting and applying an adhesive compatible with the thermoplastic surfaces of top sheet 34 and stiffener 38.

The embodiment illustrated is not intended to be exhaustive or limit the invention to the precise form disclosed. It is chosen and described in order to explain the principles of the invention and its application and practical use, and thereby enable others skilled in the art to utilize the invention.

We claim:

1. Low-cost disposable tourniquet cuff apparatus for encircling a patient's limb at a desired location on the limb to stop blood flow past the cuff, comprising:
   a first sheet formed of flexible material that is impermeable to gas;
   a second sheet formed of flexible material that is impermeable to gas and that is positioned facing the first sheet;
   a gas-tight seal joining the first sheet directly to the second sheet around a perimeter to form an inflatable bladder within the perimeter, wherein the bladder has a bladder width dimension, and a bladder length;
   securing means adapted to allow surgical staff to secure the cuff apparatus around the limb at a desired location on the limb so that the bladder overlaps upon itself;
   port means communicating with the bladder and releasably connectable to a tourniquet instrument for establishing a pneumatic passageway for pressurized gas between the bladder and the tourniquet instrument;
   a stiffener layer attached to the first sheet and sized to extend substantially the length of the bladder but not the entire bladder length, so that the entire stiffener layer is surrounded by the perimeter seal, thereby completely enclosing the stiffener layer inside of the bladder perimeter, the stiffener layer being formed of material that is less flexible than the first sheet; and
   a coating layer disposed within the bladder on one side of the stiffener layer, wherein only one of the coating layer and the stiffener layer is formed of thermoplastic material that is compatible with the material of the first sheet for welding to the first sheet, and the other one of the coating layer and the stiffener layer is formed of material that is incompatible with the material of the first sheet for welding thereto.

2. The apparatus of claim 1 wherein the stiffener layer includes a stiffener layer surface facing the second sheet, and wherein the coating layer is between the stiffener layer surface and the second sheet and is formed of a polymer having a physical property that is a barrier to molecular diffusion between the stiffener layer surface and the second sheet.

3. The apparatus of claim 2 wherein the coating layer is applied to the stiffener layer surface and the stiffener layer is formed of thermoplastic material and welded to the first sheet for attachment thereto.

4. The apparatus of claim 2 wherein the coating layer is applied to the second sheet and the stiffener layer is formed of thermoplastic material and welded to the first sheet for attachment thereto.

5. The apparatus of claim 2 wherein the coating layer is bonded to the stiffener layer and the coating layer is formed of thermoplastic material and welded to the first sheet for attachment of the coating layer and bonded stiffener layer to the first sheet.

6. The apparatus of claim 1 wherein the stiffener is sized so that no portion of the stiffener layer extends into the seal joining the first sheet and the second sheet around the perimeter.

7. The apparatus of claim 1 wherein the stiffener layer is attached to the first sheet by a weld that is separate from and spaced from the gas-tight seal joining the first sheet to the second sheet around the perimeter.

8. Low-cost tourniquet cuff apparatus for encircling a patient's limb at a desired location on the limb, comprising:
- a first sheet formed of flexible material that is impervious to gas and that includes a first thermoplastic polymer;
- a second sheet formed of flexible material that is impermeable to gas and that is positioned facing the first sheet and that includes a second thermoplastic polymer;
- a gas-tight seal joining the first sheet directly to the second sheet around a perimeter to form an inflatable bladder within the perimeter, wherein the inflatable bladder has a width and a length;
- securing means adapted to allow surgical staff to encircle the cuff apparatus around the limb at a desired location on the limb so that the bladder overlaps upon itself;
- port means communicating with the bladder and releasably connectable to a tourniquet instrument for establishing a pneumatic passageway for pressurized gas between the bladder and the connected tourniquet instrument;
- a stiffener formed of material that is less flexible than the first sheet, wherein the stiffener has a width that is less than the bladder width and a length defined between opposing ends thereof, the stiffener length extending substantially the length of the bladder but less than the bladder length, wherein the stiffener includes a first stiffener surface facing the first sheet and formed of a material that includes a thermoplastic stiffener polymer, wherein the polymers of the first stiffener surface and the first sheet have physical properties that facilitate welding together, and wherein the stiffener surface is welded to the first sheet within the bladder and away from the gas-tight seal around the perimeter; and
- barrier means contained within the bladder and adapted to prevent welding between the stiffener and the second sheet.

9. The apparatus of claim 8 wherein the stiffener is sized so that no portion of the stiffener extends into the seal joining the first sheet and the second sheet around the perimeter.

10. The apparatus of claim 8 wherein the stiffener surface is welded to the first sheet by a weld that is separate from and spaced from the gas-tight seal joining the first sheet to the second sheet around the perimeter.

* * * * *